United States Patent [19]

Baklien et al.

[11] 4,059,588
[45] Nov. 22, 1977

[54] PROCESS FOR PREPARING 6-PHENYL-2,3,5,6-TETRAHYDROIMIDAZO[2,1-b]THIAZOLE

[75] Inventors: Asbjorn Baklien, Kingsbury; Jan Kolm, Kew, both of Australia

[73] Assignee: ICI Australia Limited, Melbourne, Australia

[21] Appl. No.: 240,826

[22] Filed: Apr. 3, 1972

Related U.S. Application Data

[62] Division of Ser. No. 565,092, July 14, 1966, Pat. No. 3,759,937.

[30] Foreign Application Priority Data

| | | |
|---|---|---|
| July 19, 1965 | Australia | 61653/65 |
| July 26, 1965 | Australia | 61931/65 |
| Aug. 31, 1965 | Australia | 63415/65 |
| Sept. 8, 1965 | Australia | 63786/65 |

[51] Int. Cl.$^2$ .................................. C07D 513/04
[52] U.S. Cl. ..................................... 260/306.7 T
[58] Field of Search .................... 260/306.7, 306.7 T

[56] References Cited

U.S. PATENT DOCUMENTS 3,274,209  9/1966  Raeymaekers et al. .......... 260/306.7
3,642,809  2/1972  Bullock ........................... 260/306.7

FOREIGN PATENT DOCUMENTS 34,860  12/1964  Germany ......................... 260/306.7

Primary Examiner—R. Gallagher
Attorney, Agent, or Firm—Cushman, Darby & Cushman

[57] ABSTRACT

This disclosure relates to a process for the manufacture of compounds of the formula

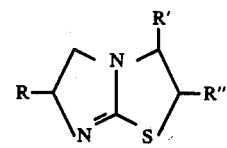

which comprises ring-closing a compound of the formula

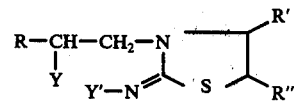

wherein the variables are as defined infra.

3 Claims, No Drawings

PROCESS FOR PREPARING 6-PHENYL-2,3,5,6-TETRAHYDROIMIDAZO[2,1-b]THIAZOLE

This application is a division of Ser. No. 565,092, filed July 14, 1966, now U.S. Pat. No. 3,759,937.

This invention relates to a new process for making chemical compounds which are useful as intermediates to biologically active compounds and/or which are themselves biologically active. It also relates to new and useful chemical compounds. One particular biological activity is the anthelmintic effect of the products of these processes.

It has been demonstrated in South African Pat. Application No. 2467/65 that certain imidazo (2,1-b) thiazoles including those having the formula

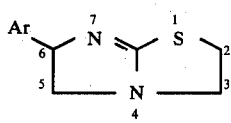

or the therapeutically acceptable acid addition salts thereof, wherein Ar is a thienyl, furyl, phenyl, halophenyl, nitrophenyl, aminophenyl, trifluoromethylphenyl, naphthyl or benzyl group, and in particular certain preferred compounds namely dl-2,3,5,6-tetrahydro-6-(4-nitrophenyl)imidazo[2,1-b]thiazole hydrochloride, dl-2,3,5,6-tetrahydro-6-(4-aminophenyl)imidazo[2,1-b]thiazole hydrochloride, dl-2,3,5,6-tetrahydro-6-phenyl-imidazo[2,1-b]thiazole hydrochloride and dl-2,3,5,6-tetrahydro-6-(2-thienyl)imidazo[2,1-b]thiazole hydrochloride have useful biological, particularly anthelmintic properties. Formulations comprising these compounds, their methods of use in combating undesired animal pests and diseases and certain process of manufacturing the compounds have also been claimed and disclosed in said patent application.

We have now discovered a process by which these and other compounds and certain intermediates useful for their synthesis may be manufactured.

Accordingly we provide a process comprising reacting a compound of the formula

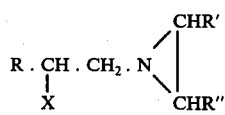 (formula I)

with a compound of the formula

 (formula II)

to produce a compound of the formula

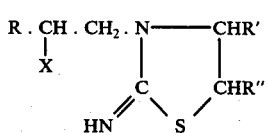 (formula III)

wherein X is hydroxy, acyloxy or hydrogen; A stands for NH₂ and D stands for hydrogen or both substituents —A and —D are absent; R, R' and R", which may be the same or different, may be hydrogen, alkyl, aryl, alkaryl or aralkyl and R may be substituted by a substituent which is non-reactive with the aziridine ring and which is halogen, nitro, acylamino, alkoxy, aryloxy, alkylthio, arylthio and wherein R furthermore may be a five- or six-membered heterocyclic radical having N, S or O in the ring and wherein R" is hydrogen whenever R' is hydrogen (Reaction 1). Typical acyloxy groups are acetoxy, propionoxy, butyroxy.

The process is of particular interest in respect of certain valuable compounds for which, as far as we know, no synthesis of comparable simplicity is known; accordingly a preferred process is characterised in that R stands for phenyl, halophenyl, nitrophenyl, trifluoromethylphenyl, naphthyl, alkoxyphenyl, alkylthiophenyl, arylthiophenyl, methyl, ethyl, benzyl, hydroxymethyl, methoxymethyl, phenoxymethyl, phenylthiomethyl, 2-thienyl, 4-pyridyl and 2-furyl; R' is hydrogen, alkyl, aryl, alkaryl or aralkyl; R" is hydrogen or, whenever R' is a substituent other than hydrogen R" may also be alkyl, aryl, alkaryl or aralkyl; and

is thiocyanic acid or isothiourea. While we consider that the latter is in this isomeric form symbolised by the formula

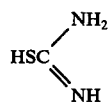

when entering in the nucleophilic attack on the aziridine ring, it will be understood that the reagent actually added is thiourea and changes to its tautomeric form in the reaction medium. Throughout this specification the terms thiourea and isothiourea are therefore used interchangeably. It is also obvious that the thiocyanic acid may be generated in situ from its salts, particularly sodium or potassium thiocyanate and a suitable acid. Our process is particularly useful for the manufacture of compounds of formula III wherein R stands for phenyl, 2- or 3- or 4-chlorophenyl, 3-bromophenyl, 4-fluorophenyl, 2-nitrophenyl, 3-nitrophenyl, 4-nitrophenyl, 4-tolyl, 3-trifluoromethylphenyl, 2,3,4-trichlorophenyl, benzyl, phenoxymethyl, phenylthiomethyl, 2-thienyl and 2-furyl and R' and R" are hydrogen.

Reaction 1 is conveniently carried out in water or in a mixture of water and a water-miscible organic solvent, in the presence of an acid. Alternatively it may also be carried out in an organic solvent in the presence of an acid which in the medium is capable of acting as a proton donor. Suitable organic solvents are e.g., lower alcohols or acetone, dioxan, tetrahydrofuran, dimethylformamide and sulpholane. Suitable acids are e.g., sulphuric, hydrochloric, nitric, perchloric, p-toluenesulphonic, phosphoric, formic, acetic, maleic, thiocyanic and oxalic acids. Excess acid, i.e., acid in excess of that required to neutralise the bases formed is preferred; two to three mole equivalents per mole of

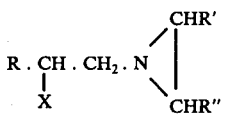

are satisfactory; 0.1 to 0.5 mole excess acid is preferred. Reactant ratios are not highly critical, but a slight excess of thiourea or thiocyanic acid respectively is preferred.

Reaction temperature for the overall reaction 1 is not narrowly critical; it varies somewhat from thiocyanic acid to thiourea and also depends on the nature of substituents R' and R''. Thus the ring-closure with thiocyanic acid occurs already at room temperature, but elevated temperatures are required with thiourea. In general best results are obtained by maintaining the temperature between −10° and 40° C over an initial period of 5 to 60 minutes, followed by heating to between 60° and 180° C for a period from ¼ to 5 hours, preferably from ¼ to 2 hours when thiocyanic acid is used and from 2 to 4 hours when thiourea is used. Higher and lower temperatures are feasible. We have isolated an intermediate in this process; hence, while we do not wish to be limited by theory, we consider that the reaction occurs in two steps; in the first step an intermediate salt is formed, namely an isothiouronium salt as exemplified in Example 32 method A whenever thiourea is used, and a thiocyanate salt of the formula

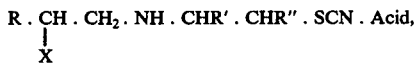

whenever thiocyanic acid is used; in the second step said intermediate salt is cyclised to the thiazolidine ring. In the case of the isothiouronium salt the intermediate salt may be isolated if desired and the two steps may be carried out separately, whereas the thiocyanate salt ring-closes more rapidly. Temperature conditions are virtually the same as when the reaction is carried out in one step; temperatures from −10° to 50° C, preferably from 5° to 30° C and reaction times from 5 to 60 minutes are used for the 1st step, the salt formation. Temperatures from 60° to 180° C are used for the second step, the ring closure; temperatures from 80° to 120° C maintained over 2–4 hours are preferred when thiourea is used, but operation above and below those temperatures is possible. In aqueous or aqueous organic media no large improvements in yield are obtained above 120° C.

Accordingly we also provide a process which comprises reacting a compound of formula I with thiourea at a temperature from −10° to 50° C, and preferably from 5° to 30° C to produce the salt of a compound of the formula

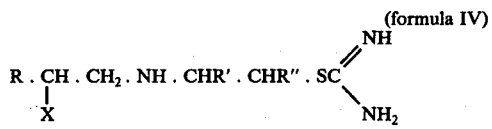

(formula IV)

wherein R, R' and R'' are as defined on page 4, lines 5–9 and X is hydroxy, acyloxy or hydrogen (Reaction 1a). Two equivalents of acid e.g. 2 HCl are bound. Suitable reaction media are as for overall reaction 1, namely water, mixed aqueous organic or an organic solvent by itself in the presence of an acid as defined.

Furthermore we provide a process which comprises ring closing a compound of formula IV at a temperature from 60° to 180° C, preferably from 80° to 120° C (Reaction 1b).

If desired the ring closure step may also be carried out in a medium different from that used in the formation of the isothiouronium salt e.g., in an organic solvent having a boiling point between 120° and 180° C, such as ethylene glycol monoacetate.

The preferred method of carrying out reaction 1 is in a single step. If in reaction 1 an acid other than the relatively strong acids listed above is used, the acidity should be adjusted to give a pH meter reading between 1 and 3.6.

The compounds of formula III may be isolated from the solvent e.g. water or alcohol, as the salt by evaporation, crystallisation or precipitation. We have found that the thiocyanic acid salt of compound III is sparingly soluble in water and in most organic solvents; the thiocyanic acid salt may be formed by adding, in reaction 1, slightly more than two equivalents of thiocyanic acid, when the latter is the reactant according to formula II, or by addition of one equivalent of thiocyanic acid to the salt of formula III after the reaction had been completed. The thiocyanate precipitates and can then be separated conveniently; when conversion to the hydrochloride salt is desired, the thiocyanate may be dried and suspended in a non-aqueous inert liquid, e.g., isopropanol and reacted with dry hydrogen chloride. The hydrochloride is obtained in high purity. Accordingly a preferred process comprises precipitating compound III as the thiocyanate. A further method of isolating compound III from aqueous media comprises forming its base by neutralising the medium to a pH of 10 to 13, extracting the base with a first water-immiscible organic solvent, e.g., chloroform, removing water from the extract, adding to the extract a second solvent which is hydrophilic and miscible with the first solvent e.g., ethanol, mixing, forming the hydrochloride by adding dry hydrogen chloride and separating the hydrochloride of compound III.

Compounds of formula III are useful as intermediates for the manufacture of anthelmintics, particularly the anthelmintics according to South African Patent Application No. 2467/65 of the formula of page 2, line 9. Many compounds of formula III are themselves useful as anthelmintics, insecticides or tickicides. The anthelmintic activity of the compounds of South African Patent Application No. 2467/65 is outstanding; thus d,1-6-phenyl-2,3,5,6-tetrahydroimidazo-(2,1-b)-thiazole hydrochloride or d,1-6-(2'-thienyl)-2,3,5,6-tetrahydro(2,1-b)-thiazole hydrochloride are fully effective against worm burdens in sheep at a concentration of 10 to 20 mg/kg of bodyweight of the sheep and even less whereas similar control with the classical anthelmintic phenothiazine can only be attained at a dosage of 600 to 800 mg/kg, i.e., at 30 to 80 times higher dosages. Other salts, particularly non-toxic addition salts, e.g., the hydrobromides, sulphates, phosphates, acetates, lactates, maleates, benzenesulphonates or the like are also contemplated and, as already disclosed in said South African Application No. 2467/65 on page 5, useful for biological applications.

We also provide a process for the manufacture of a compound of the formula (formula V)

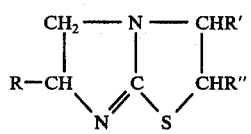

which comprises ring closing a compound of the formula (formula VI)

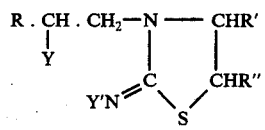

wherein Y stands for Br, Cl or acyloxy, Y' stands for acyl or hydrogen excluding, however, the case when Y is acyloxy and Y' is acyl, and wherein R, R' and R" are as defined on page 3, lines 6-12. (Reaction 2). Typical acyloxy groups are acetoxy, propionoxy and butyroxy. Ring closure is achieved by heating. When Y stands for acyloxy, heating to 150° C or more is carried out in acid medium e.g., polyphosphoric or sulphuric acid, over prolonged periods, as this reaction is slow and side reactions occur; when Y stands for Br or Cl and Y' is hydrogen or acyl, the medium may be a lower alkanoic acid anhydride e.g., acetic anhydride together with a halogenating agent $SOZ_2$, $POZ_2$ or $PZ_5$, where the halogen Z is Br or Cl; when Y stands for Br or Cl and Y' is hydrogen, the medium may also be weakly to strongly basic; at least one equivalent of an acid acceptor must be present. The base of formula VI itself may act as such an acceptor but excess alkalising agent is preferred. Good yields are obtained readily with conventional alkalising agents. The reaction with compounds in which Y stands for Cl or Br and Y' is hydrogen in the presence of an alkalising agent is preferred. Temperature for the reaction is not narrowly critical; under basic conditions the range between 40° and 150° C is suitable but 50°-80° C is preferred; below 40° C and under basic conditions the reaction proceeds, but at a slower rate. Suitable media are water, mixed aqueous organic solvents or organic solvents; suitable alkalising agents are the conventionally used basic reagents e.g., sodium bicarbonate, potassium bicarbonate, ammonium hydroxide, sodium hydroxide or potassium hydroxide; amongst these mild agents e.g., sodium bicarbonate or ammonium hydroxide are preferred.

When Y stands for Br or Cl, initially the compound of formula VI is usually present as a salt, e.g., the hydrochloride or hydrobromide; during the reaction in the presence of an alkalising agent the corresponding base and the ring-closed base are formed and when the medium is aqueous, the latter is precipitated, usually in the form of an oil.

We have now found that improved yields can be obtained in reaction 2 when an organic solvent is present which forms a separate liquid phase. Preferred solvents are the chlorinated hydrocarbons e.g., chloroform or trichloroethylene and, particularly, 1,2-dichloroethane. Accordingly a preferred process comprises ring-closing compounds of the formula VI in a medium consisting of two phases, one of which is hydrophilic, preferably aqueous and the other is an inert chlorinated hydrocarbon, preferably 1,2-dichloroethane.

We also provide a process for the manufacture of compounds of the formula (formula VII)

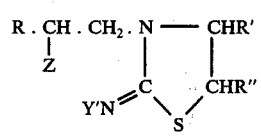

which comprises halogenating a compound of the formula (formula VIII)

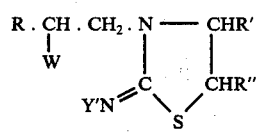

with a halogenating agent, wherein Y' is acyl or hydrogen; W is hydroxy or acyloxy; the halogenating agent may be $POZ_3$ or $PZ_5$ whenever W stands for acyloxy or hydroxy and in addition the halogenating agent may also be thionyl chloride $SOZ_2$, when W is hydroxy; the halogen Z is chlorine or bromine and R, R' and R" are as defined on page 3, lines 6-13 inclusive. (Reaction 3). The compounds of formulae VII and VIII are usually present in the form of their salts, e.g, the hydrogen halides HZ. A slight excess over the theoretical requirement of the halogenating agent, e.g, 5 to 15% molar excess is preferred.

The reaction may be carried out in any solvent which is not attacked by the halogenating agent e.g. benzene or halogenated hydrocarbons such as chloroform or methylene dichloride. A preferred solvent is 1,2-dichloroethane. Reaction temperature is not highly critical; at room temperature the reaction takes between 30 and 60 minutes, while at 50° C it proceeds more rapidly; control to between 35° and 60° C is preferred.

Furthermore we provide a process for the manufacture of compounds of the formula

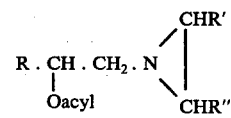

which comprises reacting a compound of the formula

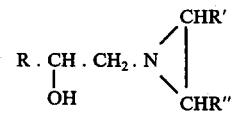

in a non-aqueous, inert solvent with a ketene, wherein R, R' and R" are as defined on page 3, line 7-12. (Reaction 4). Typical acyloxy groups are acetoxy, propionoxy or butyroxy, but acetyl is preferred and accordingly $CH_2=CO$ is the preferred ketene. The reaction temperature is not critical, preferably between 0° and 30° C; equimolar quantities of reagents or a small excess of ketene are used, but large excess of the ketene or presence of free ketene in the reaction product should be avoided since it impairs stability of compound IX. Suitable inert solvents are e.g. methylene dichloride, chloroform or diethylether.

The simplest compound according to formula I, 1-(2'-hydroxy-2'-phenylethyl)aziridine is known and may be made according to A. Funke and G. Benoit, Bulletin de la Societe Chimique de France, 1953, 1021. These authors, using ethylenimine and styrene oxide in equimolar ratios obtained yield of no more than 48%. We have repeated these experiments and have found that the material so produced is far from pure and, unless subjected to a separate purification process, is unsuitable as a starting material for Reaction 1. Impurities, particularly gums, are formed in Funke's process, presumably oligomers or polymers of either styrene or ethylenimine or of both which are difficult to remove and which contaminate the ultimate reaction products when Funke's compound is used in further reactions and render the isolation of the ultimate products difficult or inefficient. The conditions under which undesired side reactions of the two reactants, epoxides and aziridines, particularly polymerisation, can be prevented, unfortunately are in conflict; strongly alkaline conditions favour stability of the aziridines, but lead to spontaneous polymerisation of epoxides and acids polymerise or ring-open the aziridines. In addition we consider that under Funke's conditions the undesired isomer

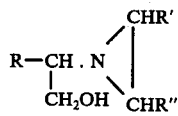

is formed which is particularly difficult to separate and to analyse. The presence of these impurities leads to further undesired by-products in subsequent reactions which cannot be readily removed or analysed and which prevent the crystallisation of the desired products. This is a serious difficulty. As far as we are aware, the synthesis of compounds of the formula V from basic chemicals currently made on technical scale has hitherto been suggested as a multistep process only. Even according to the simpler process of the present invention a 3 to 4 step synthesis is required; if in the first reaction of our combination process, the reaction between an epoxide and an aziridine, gums and impurities are formed, the crude reaction product cannot be used efficiently. It, and subsequent intermediates, must either be purified or, alternatively, yields in subsequent steps fall off rapidly. Thus, in a combination process involving 3 to 4 steps and starting from an impure first reaction product, the ultimate yield is drastically diminished, either because a sequence of purification processes involves losses, or because of low yields and difficulties with isolation.

Surprisingly we have now found that the formation of undesired impurities such as oligomers, polymers and isomers can be much reduced and a product which crystallises spontaneously may be obtained in yields in excess of 70%, and possible as high as 95% based on styrene oxide and on ethylenimine, when the reaction is carried out in a special type of polar organic solvent which is practically inert ot aziridines, preferably in the presence of catalysts.

Accordingly we provide an improved process for the manufacture of compounds of the formula

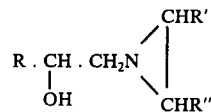

which comprises reacting an aziridine of the formula

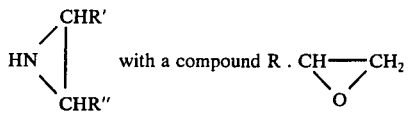

wherein R, R' and R" are as defined on page 3, lines 6–12, characterised in that the reaction is carried out in the presence of a polar organic solvent and preferably in the presence of a catalyst capable of yielding hydroxyl ions in the medium, at temperatures between 50° and 150° C, preferably 90° and 130° C, and at the corresponding equilibrium vapour pressures of the medium (Reaction 5). Suitable organic solvents are polar protic solvents, in particular ethanol and isopropanol, in the presence or absence of water. These solvents have the advantage that they are catalytic themselves and produce high reaction rates. Suitable catalysts capable of yielding hydroxyl ions are hydrolytic solvents, e.g, water, ethanol or isopropanol or strongly alkaline bases, e.g., the alkali metal hydroxides. The latter are preferred, also because their presence is desirable to prevent uncontrolled polymerisation of the aziridine. Suitable concentrations of the catalysts are from 0.0001 to 0.005 mole of catalyst per mole of epoxide. A particularly preferred polar solvent is an excess of the aziridine itself.

Accordingly we also provide a process as defined in Reaction 5 characterised in that at least 1½ molar equivalents of the aziridine are present for each molar proportion of the epoxide; we prefer to use more than 100% molar excess of the aziridine. The upper limit of excess of the aziridine is not critical; it is essentially a question of convenience and economy. Since the excess aziridine is removed after the reaction, e.g, by distillation and since little additional benefit is derived from large, say 4 or 5 molar excess of aziridine while at the same time the cost of separation and the losses on evaporation increase, large excess of ethylenimine is not favoured.

A second group of suitable solvents are the polar aprotic solvents, particularly sulpholane, dimethylformamide and dimethyl acetamide; while the reaction rate in these is slower they have the advantage of reducing the amount of the undesired isomer of the formula

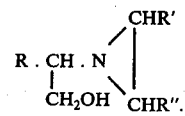

Temperatures for Reaction 5 are not narrowly critical, as indicated by the range stated above, but at the higher temperatures (90° to 130° C) shorter reaction times, between 20 and 60 minutes can be achieved. Accordingly we also prefer the corresponding slightly superatmospheric pressures.

We also provide, in combination, a process for the manufacture of a compound of formula V which comprises reacting a compound of the formula

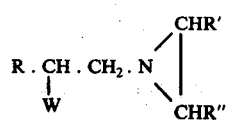
(formula IX)

with a compound of formula II as above defined to produce a compound of the formula

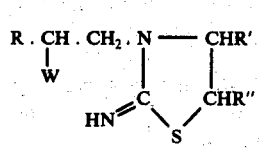
(formula X)

and ring-closing said compound of formula X, wherein R, R' and R" are as defined on page 3, lines 6–12 and W is acyloxy or hydroxy (overall reaction 6).

A preferred process of ring-closing the compound of formula X comprises displacing the group W by a substituent Z as described in Reaction 3.

An optional, less preferred variant of overall reaction 6 includes converting compound X to the acyloxy acylimine compound

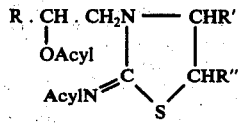

and ring closing the latter.

Furthermore we provide a process for the manufacture of compounds of formula V which comprises, in combination, the steps of reacting an aziridine of the formula

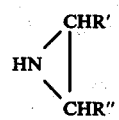

with a compound of the formula

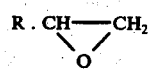

in the presence of a polar organic solvent at a temperature between 50° and 150° C, thereby obtaining a compound of the formula

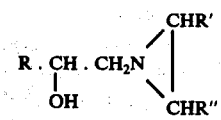

reacting the reaction product obtained without a purification step with thiourea or thiocyanic acid to obtain a compound of the formula

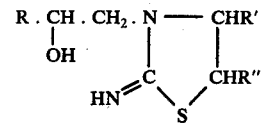

and then ring closing the compound so obtained, wherein R, R' and R", which may be the same or different, may be hydrogen, alkyl, aryl, alkaryl or aralkyl and R may be substituted by a substituent which is non-reactive with the aziridine ring and which is halogen, nitro, acylamino, alkoxy, aryloxy, alkylthio, arylthio and wherein R furthermore may be a five- or six- membered heterocyclic radical having N, S or O in the ring and wherein R" is hydrogen whenever R' is hydrogen (overall reaction 7). A preferred variant of the overall reaction 7 is the reaction wherein compound

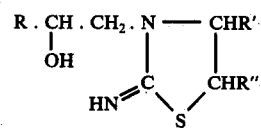

is halogenated according to reaction 3 prior closure. Another less preferred variant comprises converting the hydroxy compound of formula I to its acyloxy form prior to reaction with thiourea or thiocyanic acid.

Furthermore we provide a process for the manufacture of compounds of the formula

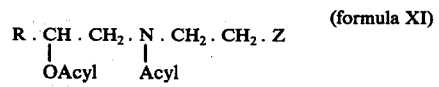
(formula XI)

which comprises reacting a compound of the formula

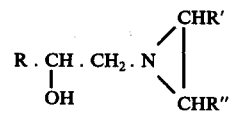

with at least two equivalents of an acyl halide e.g., $CH_3COZ$ in the presence of one equivalent of an acid acceptor, e.g. triethylamine or pyridine in an inert solvent, e.g. ether, benzene or 1,2-dichloroethane wherein R, R' and R" are as defined on page 3, lines 6–12 and Z is chlorine or bromine. Temperatures are not narrowly critical; the range from 0° to 80° C is suitable (reaction 8).

In addition we provide a process of reacting a compound of formula XI with a compound of formula II to form an intermediate of the formula

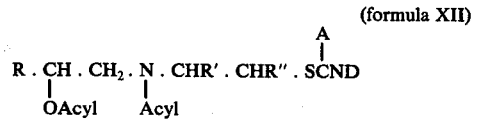
(formula XII)

and ring closing the compound of formula XII under the conditions above described for reaction 1b to form a compound of formula III wherein Z and acyl are as above defined and A, D, R, R' and R" are as defined on page 3, lines 5 to 12. (Reaction 9).

The following compounds made according to this invention are new:

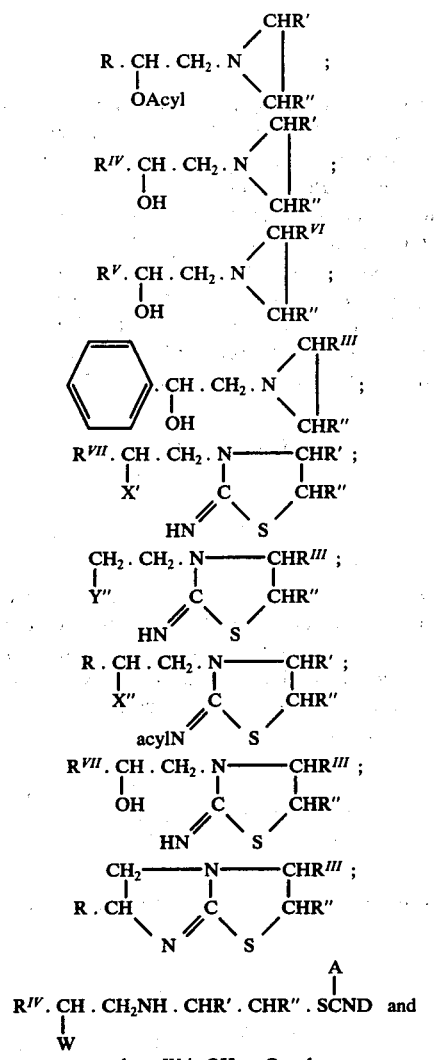

where W is OH or Oacyl;

R, R', R", A, D and X are as defined on page 3, lines 5 to 12; R$^{III}$ is alkyl, aryl, alkaryl or aralkyl; R$^{IV}$ is defined as R excluding, however, phenyl, methyl and hydrogen; R$^V$ is methyl or hydrogen; R$^{VI}$ is alkyl excluding methyl, or aryl; R$^{VII}$ is defined as R excluding, however, hydrogen; X' is H, Cl, Br or OAcyl and X" is H, Cl or Br.

Accordingly we also provide new compounds of the formula

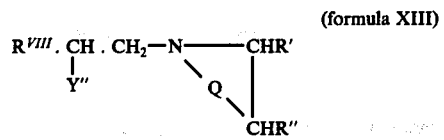
(formula XIII)

wherein Q is selected from the group consisting of Q', Q" and Q'", where Q' a direct bond to the nitrogen forming an aziridine ring, Q" is the group

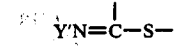

forming an minothiazolidine ring and Q'" is a monovalent radial

linked to the —CHR" group; wherein Y" is selected from the group consisting of —OH, —Oacyl, H, Cl, Br and, in the case where Q = Q", a direct link to the imino nitrogen of the thioazolidine ring; and wherein R, R', R", R$^{III}$, R$^{IV}$, R$^V$, R$^{VI}$, R$^{VII}$, A, D and Y' are as above defined, provided that:

R$^{VIII}$ equals {
R whenever Q is Q' and Y" is Oacyl;
R$^{IV}$ whenever Q is Q' and Y" is OH;
R$^V$ whenever Q is Q', Y" is OH and R' is R$^{VI}$;
phenyl whenever Q is Q', Y" is OH and R' is R$^{III}$;
R$^{VII}$ whenever Q is Q", Y" is H, Cl, Br or Oacyl and Y' is hydrogen;
hydrogen whenever Q is Q", Y' is hydrogen and R' is R$^{III}$;
R whenever Q is Q", Y" is H, Cl or Br and Y' is acyl;
R$^{VII}$ whenever Q is Q", Y" is OH, Y' is H and R' is R$^{III}$;
R whenever Q is Q", Y" is said direct link to the imine nitrogen in the thiazolidine ring and R' is R$^{III}$;
R$^{IV}$ whenever Q is Q'", Y" is OH or Oacyl and the bond between Q and N in formula XIII is replaced by a hydrogen atom attached to the nitrogen; phenyl whenever Q is Q'", Y" is OH, Oacyl or H and the bond between Q and in former XIII is replaced by a hydrogen atom attached to the nitrogen.
}

Our invention is now demonstrated by, but not limited to the examples set out below. One of the principal objects of this invention is the synthesis of compounds of formula V. The preferred combination syntheses leading to these compounds are defined by claims 29 to 30 and 31 to 34 inclusive; typical preferred syntheses of representative compounds of formula V are given in Examples 109 or 2, 38, 78, 79 or 17, 34, 76, 77 or 28, 48, 85, 86. It will be understood that various combinations of the steps according to this invention leading to compounds V are proposed; for convenience the individual steps are demonstrated in separate examples; thus e.g., reaction 5 and related syntheses are demonstrated in Examples 1 to 30; reaction 1 and related syntheses in Examples 76, 78, 84, 85, 87 and reaction 2 in Examples 75, 77, 79 to 83 etc. In these examples in many instances the isolation of intermediates is described and, in some cases, purification processes are included. It is to be understood that with intermediates this is for the purpose of identification of the compound; it does not imply that in the preferred process for making intermediates for the compounds of formula V such discrete separation of the steps is required.

On the contrary, a combination synthesis, eliminating isolation and purification steps such as e.g., after reaction 5 is envisaged in the practice of the invention, as demonstrated in Example 109 and indicated by cross references between examples.

Particularly valuable compounds of intermediate are those used in the manufacture of the known anthelmintic drug 6-phenyl-2,3,5,6-tetrahydroimidazo(2,1- b)thiazole. Thus, preferred new compounds or intermediates are those of the formulae;

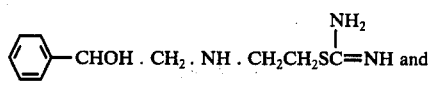

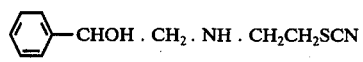

and acid-addition salts thereof, and the corresponding halogenated thiazolidines derived therefrom which are of the formula:

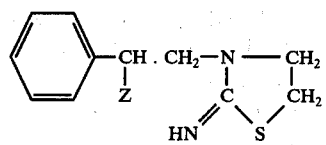

wherein Z stands for chlorine or bromine, and the acid-addition salts thereof, i.e., the compounds 2-imino-3-(2'-chloro-2'-phenylethyl)thiazolidine and 2-imino-3-(2'-bromo-2'-phenylethyl)thiazolidine and acid-addition salts thereof.

Certain of the novel compounds, indicated by certain of the formulae given on pages 15 to 17 are biologically active. Accordingly we provide biologically active compositions of matter which comprise the said novel compounds in admixture with a pharmaceutically-acceptable diluent or carrier therefor.

EXAMPLE 1

1-(2'-Hydroxy-2'-phenylethyl)aziridine (alternative name 1-hydroxy-1-phenyl-2-ethyleniminoethane)

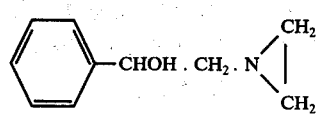

This compound was prepared as described by A. Funke, G. Benoit: Bulletin de la Societe Chimique de France 1953, 1021, from ethylenimine and styrene oxide.

The crude product obtained by this procedure was a viscous oil which did not solidify at room temperature or on prolonged cooling at 0° C. A detailed examination of the nuclear magnetic resonance spectrum of this material revealed the presence of large quantities of extraneous matter. The nuclear magnetic resonance spectrum of the pure compound obtained as decribed in Example 8 exhibits the following features: * Aziridine protons: two groups of multiplets at 1.16 and 1.72 ppm; $CH_2$ protons of the $CHOH-CH_2$ group: two sets of quadruplets at 2.16 and 2.65 ppm; CH protons: a quadruplet centred on 4.83 ppm; aromatic protons: singlet at 7.31 ppm. The nuclear magnetic spectrum of the crude material obtained by the method of the above reference showed additional broad bands extending almost continuously from 0.7 to 4.8 ppm. To test the suitability of materials obtained according to Funke, this experiment was carried out in an identical manner five times. In no case could the crude product obtained be purified by recrystallisation from ether, cyclohexane, chloroform or benzene. When the product from each of the five experiments was distilled as described in the above reference, oils were obtained in yields ranging from 45 to 52% of theory. In none of the experiments did the product solidify on standing within 48 hours; analysis of the nuclear magnetic resonance spectra showed that the distilled materials, although substantially purer than the crude materials, still contained impurities in the order of 20%.

EXAMPLE 2

1-(2'-Hydroxy-2'-phenylethyl)aziridine

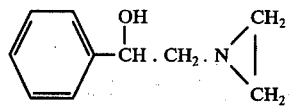

Ethylenimine (43 g), styrene oxide (120 g), ethanol (400 ml) and powdered sodium hydroxide (2g) were charged to a pressure vessel equipped with a stirrer. The vessel was immersed in an oil-bath held at 110° C and the mixture was stirred at this temperature for 2 hours. The mixture was then cooled and the alcohol distilled under reduced pressure. The remaining viscous oil was distilled in high vacuum to yield substantially pure 1-(2'-hydroxy-2'-phenylethyl)aziridine as a colourless, crystalline substance. The yield on ethylenimine and styrene oxide was 75% and purity was better than 80%. Recrystallization of a small sample from carbon tetrachloride gave colourless crystals of m.p. 77° C. This material was suitable for the synthesis of the compounds of 2-imino-3-(2'-hydroxy-2'-phenylethyl)thiazolidine and its salts as described in many of the subsequent examples, e.g., 32, 38 to 45 inclusive and 1-(2'-acetoxy-2'-phenylethyl)aziridine as described in Example 13.

EXAMPLE 3

1-(2'-Hydroxy-2'-phenylethyl)aziridine

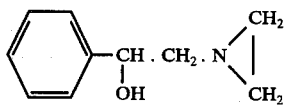

Ethylenimine (86 g = 2 moles) was heated in an autoclave to 100° C. With stirring styrene oxide (120 g) was added over 20 minutes. Stirring was continued for another 10 minutes at 100° C. Unreacted ethylenimine was then recovered first by bleeding the reactor and then by distillation at 60°–70° C and 25 mm Hg. The recovery of ethylenimine was 41.2 g or 96% of 1 mole.

The crude reaction product (165 g) solidified on cooling to room temperature. Aziridine analysis by thiosulphate titration and by nuclear magnetic resonance spectroscopy indicated 90–95% aziridine content calculated as the desired compound. Detailed analysis of the nuclear magnetic resonance spectrum and column chromatography indicated that at least 75% of the material was the desired compound. The crude reaction product was used in the synthesis of Example 39.

EXAMPLES 4 to 7 inclusive

In the same manner as described in Example 3 there were prepared the following 1-(2'-hydroxy-2'-R-ethyl) aziridines

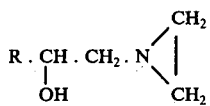

Example 4: R = m-chlorophenyl
Example 5: R = m-bromophenyl
Example 6: R = p-fluorophenyl Example 7: R = 4-thiazolyl The products of Examples 4, 5, 6 and 7 were used for the syntheses of Examples 57, 55, 58 and 62 respectively.

EXAMPLE 8

1-(2'-Hydroxy-2'-phenylethyl)aziridine

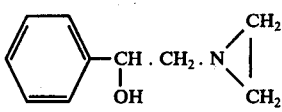

Ethylenimine (107.5 g, 2½ mole) was heated under reflux in a flask equipped with reflux condenser, stirrer, thermometer and dropping funnel. Styrene oxide (120 g = 1 mole) was added dropwise over 3 hours at a temperature between 55° C and 65° C. After the addition had been completed stirring was continued for another 3 hours at 60°-65° C. Unreacted ethylenimine was then recovered by distillation at 60° C and 10 mm Hg.

The crude reaction product (168 g) solidified on cooling. Analysis by nuclear magnetic resonance and by column chromatography indicated a purity of 83%. The crude product was used for the synthesis of Example 39.

A sample of this material was purified by recrystallisation from cyclohexane. Colourless crystals, m.p. 78°-79° C.

Another sample was recrystallised from diethyl ether. Large, waterclear crystals, m.p. 78°-79° C.

EXAMPLES 9 TO 11 INCLUSIVE

In the same manner as in Example 8 there were prepared the following 1-(2'-hydroxy-2'-R-ethyl)aziridines:

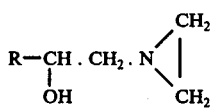

Example 9: R = m nitrophenyl
Example 10: R = 3-pyridyl
Example 11: R = m-trifluoromethylphenyl.

The products of Examples 9, 10 and 11 were used in the syntheses of Examples 53, 61 and 59 respectively.

EXAMPLE 12

1-(2'-phenylethyl)aziridine

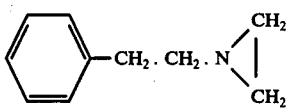

This compound was prepared in high yield as described by H. Bestian, Ann. 566, 238 (1950). B.p. 110°-114° C/10 mm Hg. This product was used for the synthesis of Example 33A and B.

EXAMPLE 13

1-(2'-Acetoxy-2'-phenylethyl)aziridine

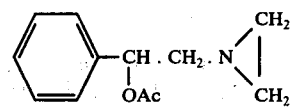

Ketene was bubbled through a solution of 1-(2'-hydroxy-2'-phenylethyl)-aziridine (10 g) in methylene chloride (20 ml) until an infra red spectrum of the solution showed no absorption due to unreacted hydroxyl. Evaporation of the solvent gave the product as a viscous oil. Distillation gave pure 1-(2'-acetoxy-2'-phenylethyl)aziridine, b.p. 111°-112° C/0.5 mm, $n_D^{20}$ 1.512. This compound was used in the synthesis of Example 69.

EXAMPLE 14

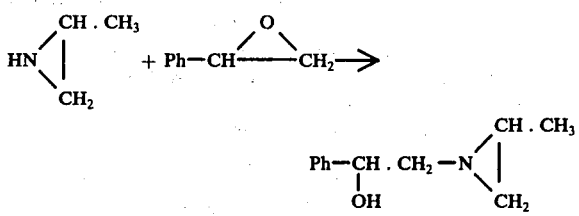

This compound was prepared from styrene oxide and propylenimine by the method described in Example 2. The product was used in the synthesis of Example 35.

EXAMPLE 15

1-(2'-Hydroxy-2'-phenylethyl)-2-(n-hexyl)aziridine

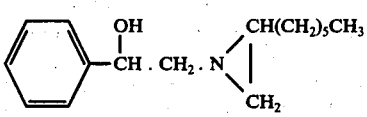

This compound was prepared from styrene oxide and 1,2-octylenimine by the method described in Example 2. The product was used in the synthesis of Example 36.

EXAMPLE 16

1-(2'-Hydroxyethyl)-2-phenylaziridine

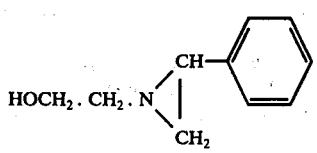

The compound was prepared from ethylene oxide and 2-phenylaziridine as described in Example 8 except that the reaction temperature was 50° C. The product was suitable for use in the synthesis according to Example 37.

EXAMPLE 17

1-[2'-Hydroxy-2'-(2''-thienyl)ethyl]aziridine

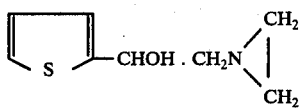

2-(Epoxyethyl)thiophene (25.2 g, prepared by the method of H. Hopff, R. Wandeler: Helv. Chim. Acta 45: 892–96 (1962)), was added dropwise over 1 hour to ethylenimine (25.8 g). The reaction mixture was stirred at 50° C during the reaction, and for 30 minutes after completed addition. Stirring was then continued for a further 1½ hour at 65° C. Excess ethylenimine was recovered by distillation at 60° C and 10 mm Hg. The crude reaction product was purified by distillation in high vacuum. B.p. 72°–76° C/0.005 mm Hg. The crude product was suitable for synthesis according to Example 34.

EXAMPLES 18 to 21 inclusive

In the same manner as in Example 17 there were prepared the following 1-(2'-hydroxy-2'-R-ethyl)aziridines of the formula

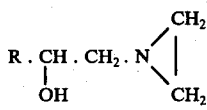

where in
  Example 18, R = 2-furyl,
  Example 19, R = 1-naphthyl,
  Example 20, R = benzyl,
  Example 21, R = p-tolyl.
The products of Examples 18, 19, 20 and 21 were used in the synthesis of Examples 51, 63, 65 and 66 respectively.

EXAMPLE 22

1-[2'-Hydroxy-2'-(4''-pyridyl)ethyl]aziridine

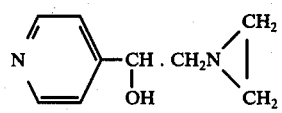

4-(Epoxyethyl)pyridine (24.2 g) was added dropwise and with stirring over 30 minutes to ethylenimine (17.2 g) at a temperarture between 55° and 65° C. After addition was completed stirring was continued at 65° C for another 2 hours. Unreacted ethylenimine was recovered by distillation at 60° C and 10 mm Hg. The residual oil was distilled in high vacuum to yield the desired product, b.p. 103°–106° C/0.01 mm Hg. The product was suitable for the synthesis described in Example 49. 4-(Epoxyethyl)pyridine was prepared by the method described by L. Polo Friz: Farmace (Pavia) Ed. Sci. 18 (12): 972–80 (1963).

EXAMPLES 23 TO 24 INCLUSIVE

In the same manner as in Example 22 there were prepared the following 1-(2'-hydroxy-2'-R-ethyl)aziridines of the formula

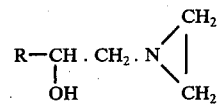

where in
  Example 23, R = o-chlorophenyl,
  Example 24. R = 2-pyridyl.
The products of Examples 23 and 24 were used in the synthesis of Examples 56 and 60.

EXAMPLE 25

1-[2'-Hydroxy-2'-(p-nitrophenyl)ethyl]aziridine

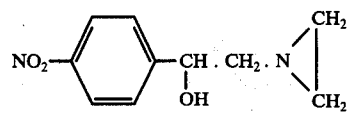

p-Nitrostyrene oxide (20.8 g) dissolved in warm dioxane was added dropwise and with stirring over 30 minutes to ethylenimine (17.2 g) at a temperature between 55° and 65° C. After the addition was completed stirring was continued at 65° C for another 2 hours. Unreacted ethylenimine and the dioxane were recovered by distillation at 60° C and 10 mm Hg. The residual oil was distilled in high vacuum to yield the desired product.
The undistilled crude product from a repeat experiment was used in the synthesis of Example 54.

EXAMPLES 26–27 inclusive

In the same manner as in Example 22 there were prepared the following 1-(2'-hydroxy-2'-R-ethyl)aziridines of the formula

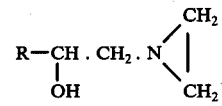

where in
  Example 26, R = o-nitrophenyl,
  Example 27, R = 2,3,4-trichlorophenyl.
The products of Examples 26 and 27 were used in the synthesis of Examples 52 and 64 respectively.

EXAMPLE 28

1-(2'-Hydroxy-3'-phenylthiopropyl)aziridine

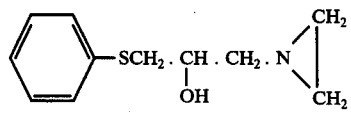

Phenyl glycidyl sulphide (33.2 g, prepared as described by H. Hopff, P. Lienhard: Helv. Chim. Acta 45, 1746 (1962)) and ethylenimine (17.2 g) were heated for 2 hours in a pressure bottle at 50°–60° C. Excess ethylenimine was removed by distillation at 55° C. and 12 mm Hg. The residual oil was distilled in high vacuum to give the desired compound as an oil, b.p. 140–144° C/0.01 mm, which crystallised in the receiver flask. Yield 26 g. (62% of theory). The structure of the compounds was confirmed by infra red and nuclear magnetic resonance spectroscopy. Infra red bands (K Br)

1478, 1433, 1258, 1105, 1089, 993, 735 and 698cm$^{-1}$. The purified compound was used in the synthesis of Examples 48.

Example 29

1-(2'-Hydroxy-3'1-phenoxypropyl)aziridine

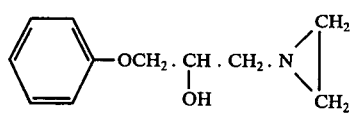

This compound was prepared by the method of Example 28. Yield 69% of theory, b.p. 132°–4° C/0.005 mm Hg. The compound was used for the synthesis of Example 67.

EXAMPLE 30

1-(2'-Hydroxy-2'-phenylethyl)-2-methylaziridine

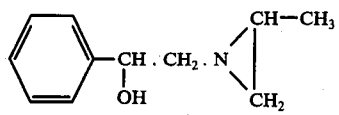

The compound was prepared by the method of Example 3. The crude product was recrystallised from cyclohexane to yield colourless crystals of m.p. 106°–108° C. Yield 63.5% of theory. The compound is suitable for the synthesis of Example 35.

EXAMPLE 31

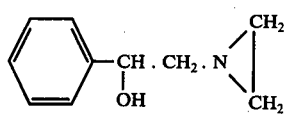

A 1.0% w/v aqueous suspension of 1-(2'-hydroxy-2'-phenylethyl)aziridine was prepared by dissolving the compound in toluene adding 5% w/v "Lubrol" E (Registered Trade Mark, a condensation product of alkyl phenol with ethylene oxide) to the solution and dispersing this concentrate in water immediately before application.

Approximately 100 larvae of the cattle tick Boophilus microplus were dipped for 5 seconds in the 1.0 w/v aqueous suspension of the compound. After 48 hours, the mortality of the larvae was 100%, whereas that of larvae dipped in a similar aqueous solution of Lubrol E was 6%.

A toxicity test on mice showed that an oral dose of 250 mg/kg of bodyweight was tolerated.

EXAMPLE 32

2-Imino-3-(2'-hydroxy-2'-phenylethyl)thiazolidine A. Method A

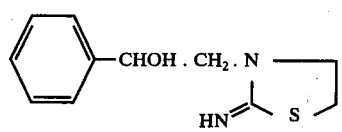

Thiourea (76 g, 1 mole) was dissolved in 1800 ml of 2N HCl and the solution was cooled to 0° C. There was then added dropwise with stirring 1-(2'-hydroxy-2'-phenylethyl)aziridine (163 g, 1 mole) dissolved in acetone. The reaction mixture was evaporated to dryness under reduced pressure to give a nearly quantitative yield of crude

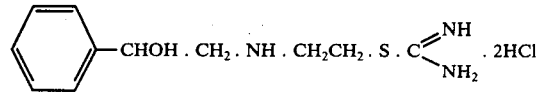

The structure was confirmed by its infra red spectrum (strong band at 1616 cm$^{-1}$). This salt was dissoled in 4 times its weight of water, the solution heated under reflux for 1 hour, evaporated in vacuo and the residue recrystallised from ethanol to yield the desired compound in 86% yield as the hydrochloride.

The hydrobromide was similarly prepared.

B. Method B

Example 32A was repeated, but instead of thiourea, 1.1 mole of potassium thiocyanate was dissolved in the hydrochloric acid and the 1-(2'-hydroxy-2'-phenylethyl)aziridine dissolved in acetone added as described. The reaction mixture was then maintained under reflux for 1 hour and evaporated to dryness. The dry residue obtained was recrystallised from methanol. The desired compound was obtained in good yield and high purity.

The experiment was then repeated, using dioxane as a solvent instead of acetone and again the desired product was obtained in good yield and purity. The compounds of Example 32A and 32B were used in the synthesis of Examples 74, 78 and 80.

EXAMPLE 33

2-Imino-2-(2'-phenylethyl)thiazolidine

A. Method A

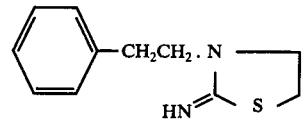

1-(2'-Phenylethyl)aziridine (147 g, 1 mole) was reacted with thiourea and the intermediate isothiourea hydrolysed as described in Example 32A to yield the desired compound as the hydrochloride in 82% yield. The free base was obtained by dissolving the hydrochloric in water and adding ammonium hydroxide with alkaline. The base separated out and was recrystallised from benzene.

B. Method B

Example 33A was repeated using instead of thiourea 1.1 mole of potassium thiocyanate. This was dissolved in the hydrochloric acid and an acetone solution of 1-(2'-phenylethyl)aziridine added as described. The mixture was refluxed for 1 hour, evaporated to dryness, the residue was recrystallised and analysed. The desired compound was obtained in fair yield and high purity.

An adult sheep infested with a wide variety of intestinal worms was dosed orally with an aqueous solution of the hydrochloride of Example 33A at the rate of 50 mg of compound per kg of bodyweight. The worm egg count before dosing was 2400 eggs per gram of faeces, whereas at 2 and 7 days after dosing it was 0 eggs per gram. There was no drop in egg count in control sheep. Mice tolerated a dose of 250 mg/kg of bodyweight.

EXAMPLE 34

2-Imino-3-[2'-hydroxy-2'-(2''-thienyl)ethyl]thiazolidine hydrochloride

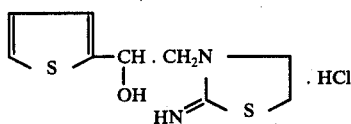

This compound was prepared by the method described in Example 48 from 16.9 g of 1-[2'-hydroxy-2'-(2''-thienyl)ethyl]aziridine. The compound was used in the synthesis of Example 76.

EXAMPLE 35

2-Imino-3-(2'-hydroxy-2'-phenylethyl)-4-methyl-thiazolidine hydrochloride

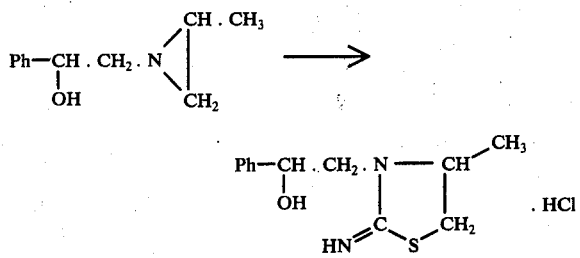

1-(2'-Hydroxy-2'-phenylethyl)-2-methylaziridine (17.7 g) was added to an ice cold mixture of 2N thiocyanic acid (50 ml) and normal hydrochloric acid (100 ml). The mixture was stirred for one hour on a steam bath. The water was removed in vacuo at 40° C and the residue crystallised from ethanol to give 2-imino-3-(2'-hydroxy-2'-phenylethyl)-4-methylthiazolidine hydrochloride. The compound was suitable for the synthesis of Example 81.

EXAMPLE 36

2-Imino-3-(2'-hydroxy-2'-phenyl)-4-n-hexylthiazolidine hydrochloride

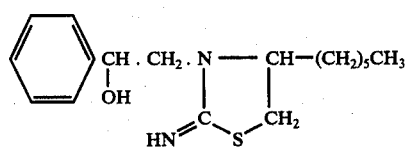

The compound was prepared by the method described in Example 39 from the compound of Example 15 and thiourea. The product was used in the synthesis of Example 82.

EXAMPLE 37

2-Imino-3-(2'-hydroxyethyl)-4-phenylthiazolidine hydrochloride

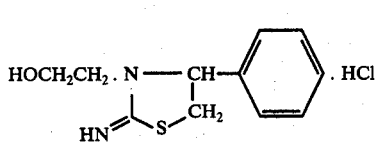

The compound was prepared as described in Example 39 from the compound of Example 16 and thiourea. The product was used in the synthesis of Example 83.

EXAMPLE 38

2-Imino-3-(2'-hydroxy-2'-phenylethyl)thiazolidine hydrochloride

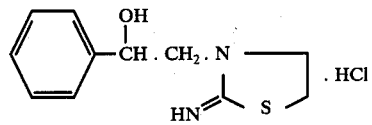

Thiourea (76 g) was dissolved in a mixture of water (1000 ml) and concentrated hydrochloric acid (175 ml). The solution was cooled to 0° C and with stirring and cooling, a solution of crude 1-(2'-hydroxy-2'-phenylethyl)-aziridine (163 g) in dioxane (200 ml) was added over a period of 1 hour. Stirring was continued for a further hour at 0° C and the mixture was then allowed to come to room temperature. It was left at room temperature for 2 hours and excess acid was then neutralised with aqueous sodium hydroxide to a pH of 3.6. The solution obtained was heated under reflux for 1½ hours and water was then removed by distillation under reduced pressure. The residue was dissolved in 400 ml of hot, absolute ethanol, filtered from undissolved ammonium and sodium chlorides and dry HCl added to the filtrate at room temperature. The mixture was then cooled until the precipitation of the desired compound was complete. The mixture was filtered and the solids washed on the filter with ice-cold absolute alcohol. 155 g of product was obtained; this was shown by nuclear magnetic resonance and infra-red spectroscopy and by thin-layer chromatography to be substantially pure. A sample was further purified by recrystallisation from absolute alcohol containing some dry HCl. White crystals, m.p. 224°–5° C.

EXAMPLE 39

2-Imino-3-(2'-hydroxy-2 '-phenylethyl)thiazolidine hydrochloride

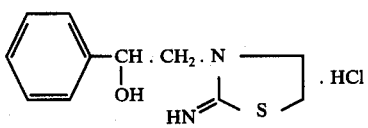

Thiourea (76 g) was dissolved with stirring in a mixture of water (700 ml) and 98% sulphuric acid (109 grams). The solution was cooled to 10° C and with stirring a solution of crude 1-(2'-hydroxy-2'-phenylethyl)aziridine (obtained by the method of Example 3) in butanol (85 ml) was added over 10 minutes, the temperature being kept below 40° C during the reaction. Stirring was continued for 15 minutes at room temperature.

The solution was heated to boiling and 100 ml of liquid phase distilled over. Boiling was then continued under reflux for a further 3 hours.

The mixture was cooled to 25°–30° C and 750 ml of chloroform were added. While the mixture was well stirred 40% aqueous sodium hydroxide was added until the pH of the solution was 11.5. The chloroform layer was separated and dried over anhydrous sodium sulphate.

Air was bubbled through the chloroform solution to remove dissolved ammonia. Absolute alcohol (80 ml) was then added and dry HCl passed until a slight excess had been added (40 g). The mixture was evaporated at 50° C over 2 hours to a volume of 350 ml. The white solid obtained was filtered off, washed with a little cold chloroform and dried. Yield of desired compound 150 g., i.e. 58% of theory based crude 1-(2'-hydroxy-2'-phenylethyl)aziridine and also 58% of theory based on styrene oxide. M.p. 222°–3° C. This product was suitable for the syntheses of Examples 74, 78 and 80.

EXAMPLE 40

2-Imino-3-(2'-hydroxy-2'-phenylethyl)thiazolidine hydrochloride

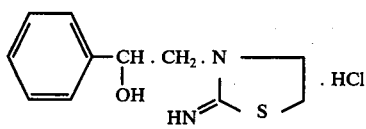

The above example was repeated using pure 1-(2'-hydroxy-2'-phenylethyl)aziridine (163 g) instead of crude, and instead of sulphuric acid, 1000 ml of water containing in solution 80 grams of HCl and 145 g of potassium chloride. The yield of product was 252.8 grams (97.8% of theoretical) m.p. 224°–5° C.

A 1.0% w/v/ aqueous solution of the compound was sprayed onto 20 adult sheep blowflies (*Lucilia cuprina*) on a piece of filter paper at the bottom of a 1lb open glass jar. After 24 hours there was 100% kill of the flies compared with 0% for flies sprayed similarly with water.

A toxicity text on mice showed that an oral does of 250 mg/kg was tolerated.

EXAMPLE 41

2-Imino-3-(2'-hydroxy-2'-phenylethyl)thiazolidine hydrochloride

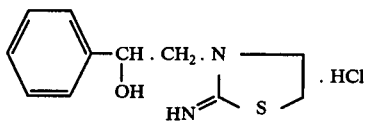

1-(2'-Hydroxy-2'-phenylethyl)aziridine (5 g) dissolved in 20 ml tetrahydrofuran was added dropwise over 75 minutes to a stirred and cooled (ice) mixture of finely powdered thiourea (2.33 g) in 120 ml of tetrahydrofuran to which had been added 10 ml of a 0.618 molar solution of dry HCl in tetrahydrofuran.

Stirring was continued for another hour. The solvent was decanted, the residue dissolved in water, the solution refluxed for 3 hours and cooled. The solution was made alkaline with aqueous sodium carbonate and the free base extracted with 150 ml chloroform, the extract dried over sodium sulphate 30 ml of isopropanol added and dry HCl introduced in slight excess. The solution was evaporated to 30 ml volume and cooled. The desired product crystallised and was collected by filtration. Yield 4.4 g = 55.2% of theory. M.p. 221°–3° C. The product was suitable for the syntheses of Examples 74, 78 and 80.

EXAMPLE 42

2-Imino-3-(2'-hydroxy-2'-phenylethyl)thiazolidine hydrochloride

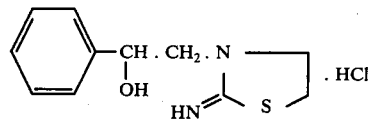

1-(2'-Hydroxy-2'-phenylethyl)aziridine (32.6 g) dissolved in 50 ml of ethanol was added dropwise over 2 hours at room temperature to a stirred mixture of finely powdered thiourea (15.2 g) in ethanol (250 ml) containing dry HCl (7.6 g).

The resulting solution was placed in an autoclave and heated at 160° C for 30 minutes. After cooling to room temperature the solution was filtered from ammonium chloride and the filtrate evaporated to about 125 ml. On cooling the desired compound crystallised. Yield 41.8 g = 81% of theory. M.p. 222°–3° C. The compound was suitable for the synthesis of Examples 74, 78 and 80.

EXAMPLE 43

2-Imino-3-(2'-hydroxy-2'-phenylethyl)thiazolidine hydrochloride

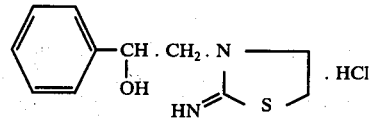

1-(2'-Hydroxy-2'-phenylethyl)aziridine (32.6 g) dissolved in 50 ml sec. butanol was added dropwise over 45 minutes at 0° to 5° C to a stirred mixture of potassium thiocyanate (20 g) in sec. butanol (300 ml) containing dry HCl (15.1 g). After completed addition, stirring was continued for another 20 minutes at room temperature. The solution was then boiled for 40 minutes during which time about half the solvent was distilled off. On cooling the desired compound crystallised. Yield 42.3 g = 82% of theory. M.p. 221°–3° C. The product was suitable for the syntheses of Examples 74, 78 and 80.

EXAMPLE 44

2-Imino-3-(2'-hydroxy-2'-phenylethyl)thiazolidine hydrochloride

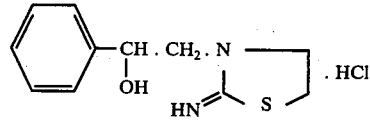

Over a period of 15 minutes 1-(2'-hydroxy-2'-phenylethyl)aziridine (5 g) was added in small portions, as a solid, to a stirred solution of thiourea (2.33 g) in water (80 ml) and 90% formic acid (4 g) at 0° to 5° C. One ml of concentrated HCl was added and the solution was refluxed for 3½ hours. The product was isolated as described in Example 39. Yield 5.5 g = 69.5% of theory. M.p. 223°–4° C. The product was suitable for the syntheses of Examples 74, 78 and 80.

EXAMPLE 45

2-Imino-3-(2'-hydroxy-2'-phenylethyl)thiazolidine hydrochloride

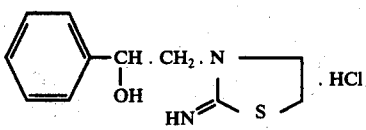

The method of Example 44 was repeated using, however, acetic acid (5.3 g) instead of formic acid. Yield of product was 5 g = 63% of theory. M.p. 222°–4° C.

EXAMPLE 46

2-Imino-3-(2'-hydroxy-2'-phenylethyl)thiazolidine hydrochloride

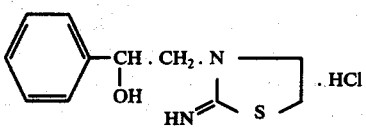

The method of Example 44 was repeated using, however, phosphoric acid (10.3 g of 88%) instead of formic acid, and omitting the addition of HCl before reflux. Yield 7.65 g = 96.5% of theory. M.p. 221°–3° C.

EXAMPLE 47

2-Imino-3-(2'-chloro-2'-phenylethyl)thiazolidine hydrochloride

The 2-imino-3-(2'-acetoxy-2'-phenylethyl)thiazolidine hydrochloride (0.01 mole) was heated under reflux with phosphorus pentachloride for one hour in chloroform (5 ml). The solvent was evaporated to leave a colourless solid which was crystallised from ethanol, yield 1.9 g. This compound was used in the synthesis of the compound of Example 75 as described for the corresponding 2-imino derivative in Example 75 Method A.

EXAMPLE 48

2-Imino-3-(2'-hydroxy-3'-phenylthiopropyl)thiazolidine hydrochloride

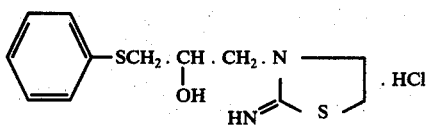

A solution of 1-(2'-hydroxy-3'-phenylthiopropyl)aziridine (26 g) in dioxan (60 ml) was added dropwise over 15 minutes and with stirring and external cooling with ice-water to a solution of thiourea (9.5 g) and concentrated hydrochloric acid (26 ml) in water (200 ml). Stirring was continued at room temperature for another 30 minutes. The solution was then heated under reflux for 3½ hours, cooled, extracted with a mixture of 15 ml n-butanol and 25 ml Chloroform, the aqueous solution made alkaline to pH 11.5 with 3N NaCH solution, and the mixture extracted twice with 75 ml portions of chloroform. The combined extracts were dried over anhydrous sodium sulphate, filtered, and ethanolic HCl was added to the filtrate until it gave an acid reaction against litmus. The solution was concentrated in vacuo. On cooling the desired product crystallised. Yield 23.2 g (61% of theory). Portion of the product was used in the synthesis of Example 84. Another portion of the sample was recrystallised from a mixture of isopropanol and ethanol (2:1 by volume). Colourless crystals, m.p. 130.5°–2° C. The structure was confirmed by infra red and nuclear magnetic resonance spectroscopy and by elemental analysis.

EXAMPLE 49

2-Imino-3-[2'-hydroxy-2'-(4''-pyridyl)ethyl]thiazolidine hydrochloride

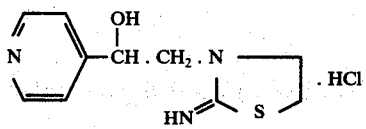

This compound was prepared by the method of Example 48. The crude dihydrochloride obtained was recrystallised from isopropanol. The product was used in the synthesis of Example 87.

EXAMPLE 50

A. 1-(2',3'-Dihydroxypropyl)aziridine

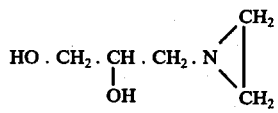

This compound was prepared from ethylenimine and 2,3-epoxypropanol by the method of Example 8, except that the temperature was held at 20° C during the addition of the epoxide. The product was used for the synthesis of Example 50B.

B. 2-Imino-3-(2',3'-dihydroxypropyl)thiazolidine hydrochloride

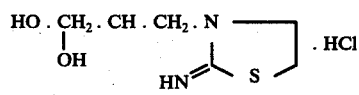

1-(2',3'-Dihydroxypropyl)aziridine was reacted with thiourea by the method of Example 39 to yield the desired compound. M.p. 188°–94° C.

EXAMPLES 51 TO 67 INCLUSIVE

The following compounds of the formula

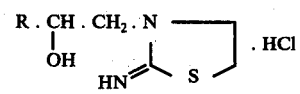

wherein R is as stated in Column 2, were prepared by the method of the corresponding example indicated in Column 3.

| Col. 1. Example No. | Col. 2 R | Col. 3 Prepared according to method of Example No. |
|---|---|---|
| 51 | 2-furyl | 34 |
| 52 | o-nitrophenyl | 39 |
| 53 | m-nitrophenyl | 39 |
| 54 | p-nitrophenyl | 39 |
| 55 | m-bromophenyl | 32A |
| 56 | o-chlorophenyl | 32A |

-continued

| Col. 1. Example No. | Col. 2 R | Col. 3 Prepared according to method of Example No. |
|---|---|---|
| 57 | m-chlorophenyl | 40 |
| 58 | p-fluorophenyl | 32B |
| 59 | m-trifluoromethylphenyl | 32A |
| 60 | 2-pyridyl | 48 |
| 61 | 3-pyridyl | 48 |
| 62 | 4-thiazolyl | 48 |
| 63 | 1-naphthyl | 32A |
| 64 | 2,3,4-trichlorophenyl | 48 |
| 65 | benzyl | 32A |
| 66 | p-tolyl | 43 |
| 67 | phenoxymethyl | 48 |

The compounds of Examples 51 to 67 inclusive were used for the syntheses of the compounds of Examples 90 to 106 inclusive.

EXAMPLE 68

2-Acetimido-3-(2'-hydroxy-2'-phenylethyl)thiazolidine

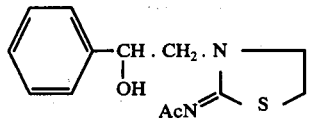

1-(2'-Hydroxy-2'-phenylethyl)aziridine (8.15 g) dissolved in 15 ml dimethyl formamide was added dropwise over 15 minutes to a stirred solution of thiourea (3.8 g) and acetic acid (6.6 g) in dimethylformamide at 0° to 10° C. The solution was filtered and heated on a steambath for 5 hours. The solvent was removed by distillation in vacuo to leave an oil. This was dissolved in a mixture of ethyl acetate and water, the organic layer separated, dried over sodium sulphate and the solvent evaporated to leave an oil which soon solidified. It was purified by recrystallisation from benzene. M.p. 99°-101° C, infra red bands at 3360, 1650, 1495cm$^{-1}$ confirmed the structure. The product was suitable for the synthesis of the product according to Example 89.

EXAMPLE 69

2-Imino-3-(2'-hydroxy-2'-phenylethyl)thiazolidine hydrochloride

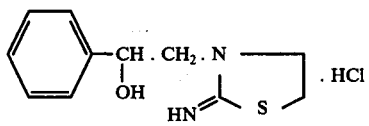

A solution of 1-(2'-acetoxy-2'-phenylethyl)aziridine (10.2 g) in acetone (5 ml) was added over 10 minutes to an ice-cold solution of thiourea (4 g) in water (100 ml) and concentrated hydrochloric acid (12 ml). The solution was stirred for 30 minutes at room temperature and then refluxed for 3½ hours. Working up as described in Example 39 gave 2-imino-3-(2'-hydroxy-2'-phenylethyl)thiazolidine hydrochloride, m.p. 217° C, identified by its infra red spectrum. The material was suitable for syntheses of the compounds of Examples 74, 78 and 80.

EXAMPLE 70

2-Imino-3-(2'-hydroxy-2'-phenylethyl)thiazolidine p-toluenesulphonate salt

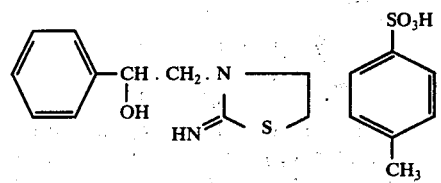

Concentrated sulphuric acid (1.56 g) was added dropwise with rapid stirring and efficient cooling in ice to a solution of ammonium thiocyanate (2.33 g) in ethanol (20 ml). The mixture was then filtered through a fluted filter paper.

A cold solution of p-toluene sulphonic acid (5.8 g) in ethanol (20 ml) was added to the filtrate, followed dropwise, with stirring and cooling, by a solution of 1-(2'-hydroxy-2'-phenylethyl)aziridine (5 g) in ethanol (20 ml). A precipitate formed during the addition. After stirring for a further 30 minutes at 0°-5° C the mixture was filtered to yield 6.9 g of the desired compound (57% of theory), m.p. 238°-40° C. The filtrate on concentration yielded a further 3.9 g of the compound.

EXAMPLE 71

A.

S-[2-(2'-Hydroxy-2'-phenylethylamino)ethyl]isothiourea bis(p-toluenesulphonate) salt

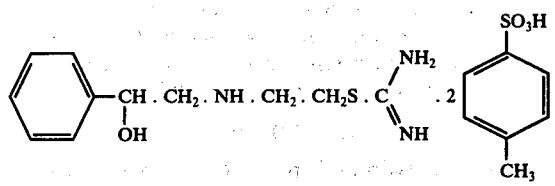

1-(2'-Hydroxy-2'-phenylethyl)aziridine (5 g) dissolved in isopropanol (30 ml) was added dropwise with stirring over 45 minutes to a mixture of finely powdered thiourea (2.33 g) and p-toluenesulphonic acid (12.2 g) in isopropanol (40 ml). The clear solution obtained was left standing for 12 hours the isothiourea salt crystallised. The product was filtered off. Further purification was not necessary. M.p. 85°-7° C. The structure was confirmed by infra red and nuclear magnetic resonance spectroscopy. A sample of this material (5.2 g) was dissolved in a small volume of water and refluxed for 3 hours. On cooling the solution deposited crystals of the compound

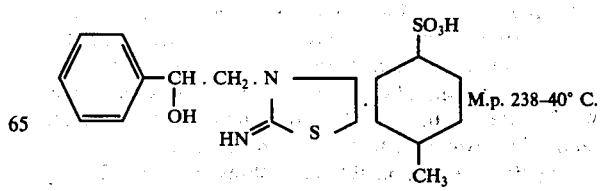

M.p. 238-40° C.

B. 2-(2'-Hydroxy-2'-phenylethylamino)ethylisothiourea dihydromaleate

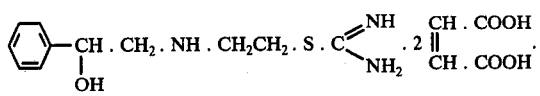

Thiourea (3.8 g) and 1-(2'-hydroxy-2'-phenylethyl)aziridine (8.7 g) were dissolved in dry methanol (60 ml) and the solution cooled to 10° C. On the addition of a solution of maleic acid (14 g) in dry methanol (20 ml) slight warming occurred, and after about 15 minutes white crystals of 2-(2'-hydroxy-2'-phenylethylamino)ethylisothiourea dihydromaleate were deposited. Filtration gave a high yield (18.9 g, ca. 74% theoretical yield) of product with m.p. 140°

C. 2-Imino-3-(2'-hydroxy-2'-phenylethyl)thiazolidine thiocyanate

A solution of 1-hydroxy-1-phenyl-2-ethyleniminoethane (16.3 g) in dioxan (35 ml) was added dropwise and with stirring at 0° C to an aqueous solution of thiocyanic acid (200 ml of 1N solution). After the addition the mixture was stirred in the cold for 1 hour. It was then heated under reflux for 1 hour and the solution cooled. The desired compound crystallised in 96% yield, m.p. 160° C.

EXAMPLE 72

2-Imino-3-(2'-hydroxy-2'-phenylethyl)thiazolidine hydrochloride

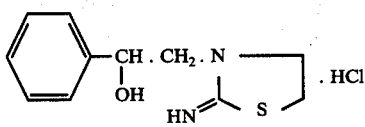

S-[2-(2'-Hydroxy-2'-phenylethylamino)ethyl]isothiouronium chloride hydrochloride (5 g, prepared as described in Example 32 Method A) was dissolved in ethyleneglycol monoacetate (8 ml) and the solution heated at 165° C for 70 minutes. After cooling the ammonium chloride formed was filtered off and the filtrate poured into diethyl ether (50 ml). The desired compound was filtered off and recrystallised from ethanol. Yield 3.1 g = 73% of theory, m.p. 222°-4° C.

EXAMPLE 73

2-Imino-3-(2'-hydroxy-2'-phenylethyl)thiazolidine hydrochloride

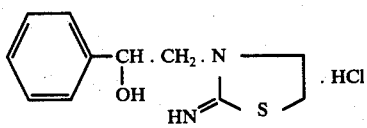

Acetyl chloride (15.7 g) in benzene (10 ml) was added dropwise with stirring and cooling over 15 minutes to a solution of 1-(2'-hydroxy-2'-phenylethyl)aziridine (16.3 g) and triethylamine (10.1 g) in benzene (90 ml). Stirring was continued at room temperature for another 40 minutes. The solution was then extracted twice with 50 ml water each time, the benzene solution dried over sodium sulphate and then filtered. The filtrate was evaporated in vacuo to leave an oil which solidified on standing. The compound, N-(2-chloroethyl)-N-(2-acetoxy-2-phenylethyl) acetamide, was purified by recrystallisation from benzene. A mixture of N-(2-chloroethyl)-N-(2-acetoxy-2-phenylethyl)acetamide (28.4 g), thiourea (8 g), concentrated hydrochloric acid (12 ml), water (250 ml) and ethanol (50 ml) was heated under reflux for 6 hours. The solution was then made alkaline with sodium hydroxide and worked up by the method of Example 39 to yield the desired compound. M.p. 222°-3° C. The compound was suitable for the synthesis of the compounds of Examples 74, 78 and 80.

EXAMPLE 74

A. 2-Imino-3-(2'-chloro-2'-phenylethyl)thiazolidine

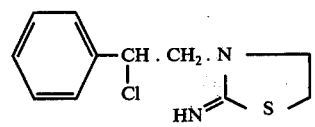

2-Imino-3-(2'-hydroxy-2'-phenylethyl)thiazolidine hydrochloride (25.85 g, 0.1 mole) was suspended in chloroform (100 ml). To the stirred mixture was added dropwise, first at room temperature, then at 50° C, thionyl chloride (12.5 g). The mixture was finally heated for 1 hour at 50° C and the solvent removed by evaporation in vacuo. The residue was recrystallised from ethanol to give the hydrochloride of the desired compound in 80% yield. The compound was suitable for the synthesis of the compound of Example 75A.

An adult sheep infested with a wide variety of intestinal worms was dosed orally with an aqueous solution of the compound at the dosage rate of 25 mg of the compound per kg of bodyweight. The worm egg count in the faeces of the sheep before dosing was 6600 eggs per gram of faeces, whereas 2 and 7 days after dosing it was 0 eggs per gram. There was no drop in the egg count of control sheep.

Four adult sheep infested with a variety of intestinal worms were dosed orally with 25 mg of the compound per kg of bodyweight. These sheep and two untreated controls were slaughtered at 5 days after dosing and the population of intestinal worms was assessed according to standard procedures as follows:

|  | *Trichostrongylus* species | *Trichostrongylus axei* | *Nematodirus* species |
|---|---|---|---|
| 1 | 20 | 140 | 560 |
| 2 | 80 | 300 | 40 |
| 3 | 20 | 120 | 0 |
| 4 | 60 | 80 | 200 |
| Control | 3440 | 200 | 3520 |
| Control | 3640 | 600 | 1640 |

A mouse treated with 250 mg/kg of bodyweight and a sheep treated with 75 mg/kg of bodyweight survived the treatment.

B. 2-Imino-3-(2'-bromo-2'-phenylethyl)thiazolidine

The bromo analogue was prepared in the same manner as under A from thionyl bromide and the hydrobromide of 2-imino-3-(2'-hydroxy-2'-phenylethyl)thiazolidine.

EXAMPLE 75

6-Phenyl-2,3,5,6-tetrahydroimidazo(2,1-b)thiazole

A. Method A

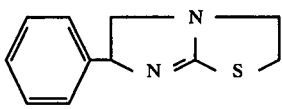

2-Imino-3-(2'-chloro-2'-phenylethyl)thiazolidine hydrochloride (27.7 g) was heated for 1 hour on a steam-bath with 200 ml of 2N sodium carbonate solution. During this time an oil formed. On cooling this solidified. It was separated and recrystallised from 20% aq. ethanol to yield the desired compound. The hydrochloride was obtained by dissolving the base in ethanol and saturating the solution with dry HCl.

B. Method B

2-Imino-3-(2'-hydroxy-2'-phenylethyl)thiazolidine hydrochloride (25.9 g) was heated in polyphosphoric acid (200 g) with stirring, at 185° C for 4 hours. The mixture at 100° C was poured with stirring into 1 liter of water, the solution made alkaline with sodium hydroxide and the product extracted with chloroform. Evaporation of the solvent left the desired product as the free base.

EXAMPLE 76

2-Imino-3-[2'-chloro-2'-(2"-thienyl)ethyl]thiazolidine hydrochloride

Example 74A was repeated as described above using, however, 2-imino-3-[2'-hydroxy-2'-(2"-thienyl)-ethyl]thiazolidine hydrochloride (26.45 g, 0.1 mole) instead of 2-imino-3-(2'-hydroxy-2'-phenylethyl)thiazolidine hydrochloride. The desired product was obtained in fair yield and purity and was used for the synthesis of Example 77.

EXAMPLE 77

6-(2'-Thienyl)-2,3,5,6-tetrahydroimidazo(2,1-b)thiazole

The product obtained in Example 76 was heated for 1 hour on a steam-bath with 200 ml of 2N sodium carbonate solution. During this time an oil formed. On cooling this solidified. It was separated and recrystallised from 20% aq. ethanol to yield the desired compound. The hydrochloride was obtained by dissolving the base in ethanol and saturating it with dry HCl.

EXAMPLE 78

2-Imino-3-(2'-chloro-2'-phenylethyl)thiazolidine hydrochloride

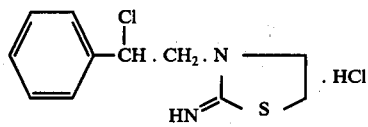

2-Imino-3-(2'-hydroxy-2'-phenylethyl)thiazolidine hydrochloride (258.5 g) was suspended in 1500 ml of chloroform. The mixture was vigorously stirred and maintained at 35° C while thionyl chloride (120 g) was added dropwise over a period of 1 hour. Stirring was continued for another hour at 35°-40° C. The mixture was then cooled to room temperature and the crude reaction product removed by filtration. It was washed with chloroform and dried to give 251 g of the desired compound in better than 90% purity. Recrystallisation of a sample from absolute ethanol containing dry HCl gave colourless crystals of m.p. 205°-8° C. The crude product was suitable for ring closure as described in Example 79.

EXAMPLE 79

6-Phenyl-2,3,5,6-tetrahydroimidazo(2,1-b)thiazole hydrochloride

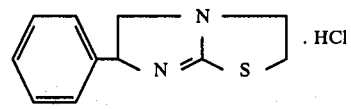

The product from Example 78 was converted to the desired 6-phenyl-2,3,5,6-tetrahydroimidazo(2,1-b)thiazole hydrochloride and recrystallised as described in Example 75A. 168 g of substantially pure product, m.p. 255°-6° C, was obtained.

Examples 2, 38, 78 and 79 in sequence demonstrate a preferred sequence of processes to synthesise 6-phenyl-2,3,5,6-tetrahydroimidazo(2,1-b)thiazole hydrochloride.

EXAMPLE 80

6-Phenyl-2,3,5,6-tetrahydroimidazo(2,1-b)thiazole hydrochloride

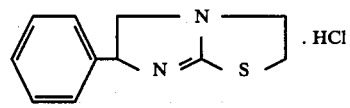

2-Imino-3-(2'-hydroxy-2'-phenylethyl)thiazolidine hydrochloride (258.5 g) was suspended in 1000 ml of 1,2-dichloroethane (EDC). The mixture was heated to 40° C and with stirring thionyl chloride (132 g) was added over 10 minutes. Stirring was continued at 40° C until no more gas was evolved. Cold water (500 ml) was then added slowly, with stirring followed by a slow addition of solid sodium bicarbonate (520 g). The mixture was then heated to 60° C, with stirring, and held at this temperature until no more gas was evolved (1½ hours). The reaction mixture was cooled to room temperature and the EDC layer separated and dried over soda ash. The soda ash was washed with two lots of 250 mls EDC. The aqueous layer was extracted with two lots of 250 ml EDC and the soda ash was further washed, successively, with these extracts. Dry HCl (40 g) was next passed into the EDC solution. The solution was heated to boiling and 50 ml of EDC distilled off. On cooling the required compound crystallised in high purity. Yield 226 g (94% of theory), m.p. 253°-4° C.

EXAMPLE 81

3-Methyl-6-phenyl-2,3,5,6-tetrahydroimidazo(2,1-b)thiazole hydrochloride

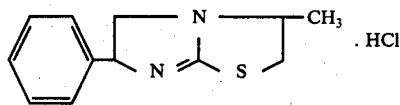

2-Imino-3-(2'-hydroxy-2'-phenylethyl)-3-methyl-thiazolidine hydrochloride (9.4 g) was reacted with thionyl chloride by the method of Example 80. The hydrochloride was obtained in 77% yield.

A 1.0% w/v aqueous solution of the hydrochloride containing in addition 0.25% w/v Lubrol E (Registered Trade Mark, a condensation product of alkyl phenol with ethylene oxide) was applied as single drops through a micro-syringe (0.15 mm internal bore needle) onto the ventral portion of 50 individual engorged female cattle ticks (*Boophilus microplus*). After 14 days the mortality of these ticks was 98%, whereas that of control ticks dipped in 0.25% w/v aqueous "Lubrol" E was 4%.

A toxicity test on mice showed that an oral dose of 250 mg/kg was tolerated.

EXAMPLE 82

3-Hexyl-6-phenyl-2,3,5,6-tetrahydroimidazo(2,1-b)thiazole hydrochloride

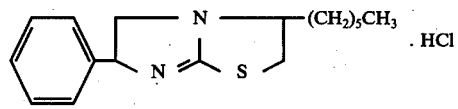

This compound was prepared from 2-imino-3-(2'-hydroxy-2'-phenylethyl)-4-hexylthiazolidine hydrochloride by the method of Example 80.

EXAMPLE 83

3-Phenyl-2,3,5,6-tetrahydroimidazo(2,1-b)thiazole hydrochloride

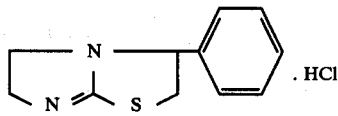

2-Imino-3-(2-hydroxyethyl)-4-phenylthiazolidine hydrochloride was reacted with thionyl bromide by the method of Example 85 and the product was cyclised by the method of Example 86.

EXAMPLE 84

2-Imino-3-(2'-chloro-3'-phenylthiopropyl)thiazolidine hydrochloride

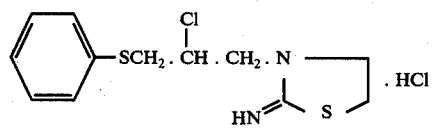

2-Imino-3-(2'-hydroxy-3'-phenylthiopropyl)thiazolidine hydrochloride (5 g) was suspended in 50 ml of chloroform and thionyl chloride (5 ml) added all at once, with stirring. After 20 minutes the solution was evaporated to dryness in vacuo and recrystallised twice from isopropanol. Yield 3.81 g = 72% of theoretical. M.p. 165°–176° C. The structure was confirmed by infra red and nuclear magnetic resonance spectroscopy and by elemental analysis.

EXAMPLE 85

2-Imino-3-(2'-bromo-3'-phenylthiopropyl)thiazolidine

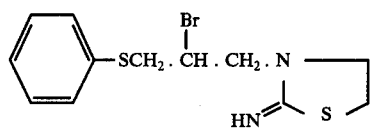

2-Imino-3-(2'-hydroxy-3'-phenylthiopropyl)thiazolidine hydrochloride (5 g) was suspended in 50 ml ethylene dichloride and thionyl bromide (5 ml) in ethylene dichloride (10 ml) was added dropwise with stirring over 20 minutes. Stirring was continued for another 30 minutes. Water (50 ml) was added slowly followed by excess solid sodium hydrogen carbonate. The temperature was not allowed to rise above 30° C. After stirring for 10 minutes the organic layer was separated, and the solvent removed at 30° C in a rotary evaporator to leave the desired compound as a crude solid. A sample was purified by crystallisation from ethanol and its structure confirmed by infra red and nuclear magnetic resonance spectroscopy and by elemental analysis. The crude product was suitable for the synthesis of Example 86.

EXAMPLE 86

6-Phenylthiomethyl-2,3,5,6-tetrahydroimidazo(2,1-b)thiazole hydrobromide

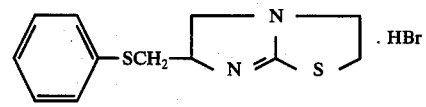

2-Imino-3-(2'-bromo-3'-phenylthiopropyl)thiazolidine (3.31 g) was dissolved in dimethylformamide (10 ml) and the solution heated on a water bath for 1½ hours. On cooling, some of the hydrobromide crystallised and a further quantity was obtained by pouring the filtrate into dioxan (50 ml). The product was recrystallised from isopropanol.

An adult sheep infested with a wide variety of intestinal worms was dosed orally with an aqueous solution of the compound at the dosage rate of 25 mg of the compound per kg of bodyweight. The worm egg count in the faeces of the sheep before dosing was 7000 eggs per gram of faeces, whereas at 2 and 7 days after dosing it was 0 eggs per gram. There was no drop in egg count in control sheep.

EXAMPLE 87

2-Imino-3-[2'-chloro-2'-(4"-pyridyl)ethyl]thiazolidine dihydrochloride

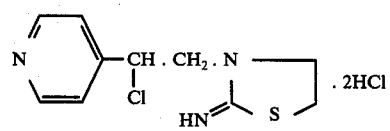

This compound was prepared from 2-imino-3-[2'-hydroxy-2'-(4"-pyridyl)ethyl]thiazolidine dihydrochloride by the method of Example 84.

EXAMPLE 88

6-(4'-Pyridyl)-2,3,5,6-tetrahydroimidazo(2,1-b)thiazole dihydrochloride

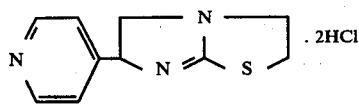

2-Imino-3-[2'-chloro-2'-(4''-pyridyl)ethyl]thiazolidine dihydrochloride (2.79 g) was suspended in 50 ml chloroform and an aqueous solution of sodium hydrogen carbonate added in excess. The mixture was vigorously stirred at 60° C for 2 hours. The chloroform layer was separated, dried over sodium sulphate, 10 ml of isopropanol saturated with dry HCl added and the solution obtained concentrated to a volume of 15 ml. On cooling the salt crystallised.

EXAMPLE 89

A.
2-Acetimino-3-(2'-chloro-2'-phenylethyl)thiazolidine

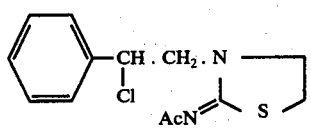

2-Acetimino-3-(2'-hydroxy-2'-phenylethyl)thiazolidine (26 g) was reacted with thionyl chloride by the method described in Example 74A to yield the desired compound which was purified by recrystallisation from benzene. The product was used for the synthesis of the compound of Example 89B.

B. 6-Phenyl-2,3,5,6-tetrahydroimidazo(2,1-b)thiazole hydrochloride

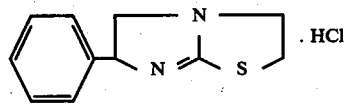

A mixture of 2-acetimino-3-(2'-chloro-2'-phenylethyl)-thiazolidine (14 g), thionyl chloride (35 g) and acetic anhydride (90 g) was stirred and heated under reflux for 45 minutes. The acetyl chloride formed was then distilled off together with unreacted acetic anhydride (under reduced pressure). The residue was dissolved in dilute hydrochloric acid, filtered, and the filtrate made alkaline to pH 11 and worked up as described in Example 39 to yield the desired compound. M.p. 251°-5° C.

EXAMPLES 90 to 106 inclusive

The following compounds of the formula

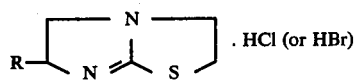

where R is as stated in column 2, were prepared by the methods indicated according to the examples in column 3.

| Col. 1 Example No. | Col. 2 R | Col. 3 Prepared according to Example No. |
|---|---|---|
| 90 | 2-furyl | 80 |
| 91 | o-nitrophenyl | 80 |
| 92 | m-nitrophenyl | 80 |
| 93 | p-nitrophenyl | 80 |
| 94 | m-bromophenyl | 80 |
| 95 | o-chlorophenyl | 80 |
| 96 | m-chorophenyl | 80 |
| 97 | p-fluorophenyl | 80 |
| 98 | m-trifluoromethylphenyl | 80 |
| 99 | 2-pyridyl (2HCl) | 88 |
| 100 | 3-pyridyl (2HCl) | 88 |
| 101 | 4-thiazolyl (2HCl) | 88 |
| 102 | 1-naphthyl | 80 |
| 103 | 2,3,4-trichlorophenyl | 80 |
| 104 | benzyl (HBr) | 85 |
| 105 | p-tolyl | 80 |
| 106 | phenoxymethyl (HBr) | 85 |

EXAMPLE 107

A. Styrene oxide (12.0 g) and ethylenimine (4.3 g) were reacted according to A. Funke, G. Benoit: Bulletin de la Societe Chimique de France 1953, 1021.

B. The crude reaction product was dissolved in n-butanol (20 ml) and reacted with thiourea by the method described in Example 32A. The crude product obtained was a viscous oil which did not solidify and could not be purified by crystallisation. The infra red and nuclear magnetic resonance spectra were very complex and could not be interpreted and the presence of the desired compound could not be asserted on the basis of these spectra.

The crude material was then reacted with thionyl chloride by the method of Example 74, but again no product could be isolated or purified.

When this material was reacted with sodium carbonate as described in Example 75A the final product was a viscous, sticky mass which did not crystallise and which could not be purified by crystallisation. The infra red and nuclear magnetic resonance spectra could not be interpreted and did not indicate the presence in the material of the desired compound, 6-phenyl-2,3,5,6-tetrahydroimidazo(2,1-b)thiazole hydrochloride.

C. Experiment B was repeated using however the reaction conditions of Example 39 instead of 32A. The result was the same as in Experiment B above.

D. Experiment B was repeated using however the reaction conditions of Example 42 instead of Example 32A; the result was again as in Experiment B above.

E. Experiment B was repeated using, however, thiocyanic acid instead of thiourea and the reaction conditions of Example 32B instead of Example 32A the experiment again failed to produce the desired compound, as in Experiment B above.

F. Experiment E was repeated using, however, the reaction conditions of Example 43 instead of Example 32B, with the same negative result.

In none of these experiments did the crude product of Funke and Benoit lead to any identifiable compounds.

EXAMPLE 108

A. Styrene oxide (120 g) and ethylenimine (43 g) were reacted according to A. Funke, G. Benoit (loc. cit.) and the crude product distilled in vacuo to yield a viscous oil which did not solidify but which was shown by infra red and nuclear magnetic resonance spectroscopy to be of much better purity than the crude product. Yield of oil was 83 g (51% of theory).

B. This oil (16.3 g) was reacted with thiourea by the method of Example 39 to give 2-imino-3-(2'-hydroxy-2'-phenylethyl)thiazolidine hydrochloride in a yield of 18.6 g (72% of theory based on the oil, or 36.7% of theory based on styrene oxide or ethylenimine).

C. This material (18.6 g) was then reacted with thionyl chloride by the method of Example E. The intermediate chloro-compound was not purified but cyclised according to the method of Example 75A to yield purified 6-phenyl-2,3,5,6-tetrahydroimidazo(2,1-b)thiazole hydrochloride, 13.9 g (79% of theory based on 2-imino-3-(2'-hydroxy-2'-phenylethyl)thiazolidine hydrochloride, 29% based on styrene oxide). The total synthesis described in this example steps A to C was carried out three times. The overall yield from styrene oxide to 6-phenyl-2,3,5,6-tetrahydroimidazo(2,1-b)-thiazole hydrochloride was in no case better than 29%.

EXAMPLE 109

6-Phenyl-2,3,5,6-tetrahydroimidazo(2,1-b)thiazole

A. Ethylenimine (86 g = 2 moles) was heated in an autoclave to 100° C. With stirring styrene oxide (120 g) was added over 20 minutes. Stirring was continued for another 10 minutes at 100° C. Unreacted ethylenimine was then recovered first by bleeding the reactor and then by distillation at 60°-70° C and 25 mm Hg. The recovery of ethylenimine was 41.2 g or 96% of 1 mole.

The crude reaction product (165 g) solidified on cooling to room temperature.

B. Thiourea (76 g) was dissolved with stirring in a mixture of water (700 ml) and 98% sulphuric acid (109 grams). The solution was cooled to 10° C and with stirring a solution of crude 1-(2'-hydroxy-2'-phenylethyl)aziridine (obtained as described in Example 109 A in butanol (85 ml) was added over 10 minutes, the temperature being kept below 40° C during the reaction. Stirring was continued for 15 minutes at room temperature.

The solution was heated to boiling and 100 ml of liquid phase distilled over. Boiling was then continued under reflux for a further 3 hours.

The mixture was cooled to 25°-30° C and 750 ml of chloroform were added. While the mixture was well stirred 40% aqueous sodium hydroxide was added until the pH of the solution was 11.5. The chloroform layer was separated and dried over anhydrous sodium sulphate.

Air was bubbled through the chloroform solution to remove dissolved ammonia. Absolute alcohol (80 ml) was then added and dry HCl passed until a slight excess had been added (40 g). The mixture was evaporated at 50° C over 2 hours to a volume of 350 ml. The white solid obtained was filtered off, washed with a little cold chloroform and dried. Yield of desired compound 150 g, i.e., 58% of theory based on crude 1-(2'-hydroxy-2'-phenylethyl)aziridine and also 58% of theory based on styrene oxide. M.p. 222°-3° C.

C. The product from Example 109B (150 g) was suspended in 580 ml of 1,2-dichloroethane (EDC). The mixture was heated to 40° and with stirring thionyl chloride (77 g) was added over 10 minutes. Stirring was continued at 40° C until no more gas was evolved. Cold water (290 ml) was then added slowly, with stirring followed by a slow addition of solid sodium bicarbonate (300 g). The mixture was then heated to 60° C, with stirring, and held at this temperature until no more gas was evolved (1½ hours). The reaction mixture was cooled to room temperature and the EDC layer separated and dried over soda ash. The soda ash was washed with two lots of 145 ml EDC. The aqueous layer was extracted with two lots of 145 ml EDC and the soda ash was further washed, successively, with these extracts. Dry HCl (24 g) was next passed into the EDC solution. The solution was heated to boiling and 30 ml of EDC distilled off. On cooling the required compound crystallised. Yield 132 g (94% of theory based on the product of Example 109B and 54.5% of theory based on styrene oxide). M.p. 252°-5° C.

What is claimed is:

1. A process which comprises contacting an acid addition salt of a compound of the formula:

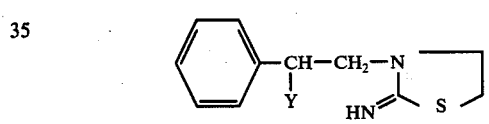

wherein Y is halogen, with an aqueous alkaline solution, heating the mixture at a temperature in the range between 40° and 150° C. to cause the formation of the free base of the dl 6-phenyl-2,3,5,6-tetrahydroimidazo[2,1-b]thiazole, as a separate phase separating the separate phase and recovering said product therefrom.

2. A process according to claim 1, wherein Y is chlorine.

3. A process according to claim 1, wherein Y is bromine.